United States Patent [19]
O'Brien

[11] Patent Number: 5,213,815
[45] Date of Patent: May 25, 1993

[54] TREATMENT OF ASCITES IN POULTRY

[76] Inventor: Gerard T. O'Brien, 2162 Sylite Dr., Gainesville, Ga. 30501

[21] Appl. No.: 774,785

[22] Filed: Oct. 10, 1991

[51] Int. Cl.$^5$ ............................................. A01N 00/01
[52] U.S. Cl. .................................. 424/935; 424/195.1
[58] Field of Search ...................... 424/684, 935, 135.1

[56] References Cited

U.S. PATENT DOCUMENTS 4,719,111  1/1988  Wilson .............................. 514/925

Primary Examiner—Douglas W. Robinson
Assistant Examiner—Deborah Hung

[57] ABSTRACT

A method of treating ascites in poultry comprising administering Eyebright herb and Brewer's yeast to poultry in need thereof. The Brewer's yeast and eyebright quantities ingested by the birds can be varied judiciously to suit the poultry breed, the severity of the environmental conditions and the severity of the diseased condition of the stricken birds.

1 Claim, No Drawings

TREATMENT OF ASCITES IN POULTRY

BACKGROUND OF THE INVENTION

Ascites syndrome poses a serious problem to young fast-growing poultry all over the world. The syndrome is usually manifested by an excessive accumulation of serum like fluid in the abdomen of the bird. Death from ascites results due an enlarged heart, liver damage, kidney, lung and intestinal problems. Mortality to United States poultry flocks can amount to 2% of birds "started". This results in multimillion dollars lost due to ascites. In some cases, at high altitude, deaths from ascites has amounted to over 30%.

Recently there has been a marked increase in the incidence of ascites in low altitude countries such as the United Kingdom, Italy, Germany, Australia and Mauritius. Male birds are at greater risk than females. Mortalities increase substantially during colder temperatures. In some cases, 50% of all broiler mortalities over 2 weeks of age were due to ascites during the winter months. Recent evidence tends to show that ascites is now increasing during warmer weather and is now appearing at a younger age in the poultry.

Brewer's yeast is a by product of the brewery operation, and is a waste product and is plentiful and cheap. The herb eyebright, *Euphrasia officinalis*, has traditionally been used as a remedy for eye problems.

SUMMARY OF THE INVENTION

This invention is directed to the treatment and prevention of ascites in poultry. In order to prevent the disease of ascites in poultry, Brewer's yeast is added to the poultry food at a rate of about 40 grams per 160 pounds of poultry weight per day. This is continued from "day old" through the last day of "grow out". In order to treat ascites in poultry the herb "Eyebright" is added, in addition to the Brewer's yeast, to the poultry food at a rate of about 500 milligrams per 160 pounds of poultry per day for a period of 7 days. The relative amounts of Brewer's yeast and Eyebright can be varied up and down in quantity to suit the poultry breed and severity of the environmental conditions and the disease.

It is preferred that the stricken poultry be penned separately from the rest of the poultry during the treatment period. The Brewer's yeast should be administered on a constant basis from day 1 and the Eyebright administered for a 1 week period. The poultry should be returned to the main flock on being cured.

I claim:

1. A method of treating ascites in poultry comprising administering a therapeutically effective quantity of Eyebright herb in combination with a preventive quantity of Brewers yeasts to poultry in need thereof,
    wherein the Brewer's yeast is administered in a mixture with the poultry food or water at a rate of about 40 grams per day per 160 pounds of poultry, and
    wherein the Eyebright herb is administered in a mixture with the food or water at a rate of about 500 milligrams per day per 160 pounds of poultry.

* * * * *

UNITED STATES PATENT AND TRADEMARK OFFICE
CERTIFICATE OF CORRECTION

PATENT NO. : 5,213,815
DATED : May 25, 1993
INVENTOR(S) : Gerard T. O'Brien

It is certified that error appears in the above-indentified patent and that said Letters Patent is hereby corrected as shown below:

On the title page, item (76), change "Sylite" to --Skyline--.

Column 2, line 2, change "grams" to --grains--.

Column 2, line 27, change "grams" to --grains--.

Signed and Sealed this

Nineteenth Day of October, 1993

*Attest:*

BRUCE LEHMAN

*Attesting Officer*     *Commissioner of Patents and Trademarks*